(12) United States Patent
Vitek et al.

(10) Patent No.: US 6,436,996 B1
(45) Date of Patent: *Aug. 20, 2002

(54) MODULATION OF NITRIC OXIDE PRODUCTION

(75) Inventors: Michael P. Vitek, Apex, NC (US); Carol A. Colton, Silver Spring, MD (US)

(73) Assignees: Duke University, Durham, NC (US); Georgetown University, Washington, DC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/940,594

(22) Filed: Sep. 30, 1997

(51) Int. Cl.[7] ..................... A61K 31/195; A61K 31/21; A61K 31/16; A61K 31/04
(52) U.S. Cl. ..................... 514/565; 514/506; 514/561; 514/625; 514/626; 514/627; 514/706; 514/742; 514/724; 514/747
(58) Field of Search ........................... 514/561, 742, 514/565, 724, 747, 706, 625, 626, 627, 506

(56) References Cited

U.S. PATENT DOCUMENTS

| | | | |
|---|---|---|---|
| 5,543,430 A | 8/1996 | Kaesemeyer | 514/565 |
| 5,585,402 A | 12/1996 | Moncada et al. | 514/564 |
| 5,658,565 A | 8/1997 | Billiar et al. | 424/93.21 |
| 5,747,545 A | * 5/1998 | Lipton | 514/742 |

FOREIGN PATENT DOCUMENTS

| | | |
|---|---|---|
| WO | WO 93/20088 | 10/1993 |
| WO | WO 97/33609 | 9/1997 |

OTHER PUBLICATIONS

Riddell et al.; Apolipoprotein E Inhibits Platelet Aggregation through the L–Arginine: Nitric Oxide Pathway, Implications for Vascular Disease, Abstract XP–002093544, *The J. of Biological Chemistry*, 272(1):89–95 (1997).

Strittmatter et al.; Binding of Human Apolipoprotein E to Synthetic Amyloid βPeptide: Isoform–Specific Effects and Implications for Late–Onset Alzheimer Disease, Abstract XP–002093545, *Proc. Natl. Acad. Sci., USA*, 90:8098–8102 (1993).

Meda et al.; Activation of Microglial Cells by β–Amyloid Protein and Interferon–$\gamma$, Abstract XP–002093546, *Nature*, 374:647–650 (1995).

Miyata et al.; Apolipoprotein E Allele–Specific Antioxidant Activity and Effects on Cytotoxicity by Oxidative Insults and β–Amyloid Peptides, Abstract XP–002093547, *Nature Genetics*, 14(1):55–61 (1996).

Barger et al.; Microglial Activation by Alzheimer Amyloid Precursor Protein and Modulation by Apolipoprotein E, Abstract XP–002093548, *Nature*, 388:878–881 (1997).

Vitek et al.; Modulation of Nitric Oxide Production in Human Macrophages by Apolipoprotein–E and Amyloid–Beta Peptide, Abstract XP–002093549, *Biochemical and Biophysical Research Communications*, 240:391–394, Journal Code: 9Y8, Issn: 0006–291X (1997).

PCT International Search Report of PCT/US98/20412, filed Sep. 30, 1998.

* cited by examiner

*Primary Examiner*—Theodore J. Criares
(74) *Attorney, Agent, or Firm*—Myers Bigel Sibley & Sajovec

(57) ABSTRACT

A method of treating cells that carry at least one APOE4 allele comprises increasing nitric oxide levels in the cells (e.g., by administering an exogenous source of nitric oxide to the cells) by an amount sufficient to combat the decrease of nitric oxide level associated with the presence of the APOE4 allele. Also disclosed is a method of increasing nitric oxide levels in cells in need thereof which comprises administering APOE to the cells in an amount sufficient to increase nitric oxide levels in the cells.

14 Claims, 3 Drawing Sheets

Figure 1. The effect of apolipoprotein-E on nitrite production in cultured human monocyte-derived macrophage cells.
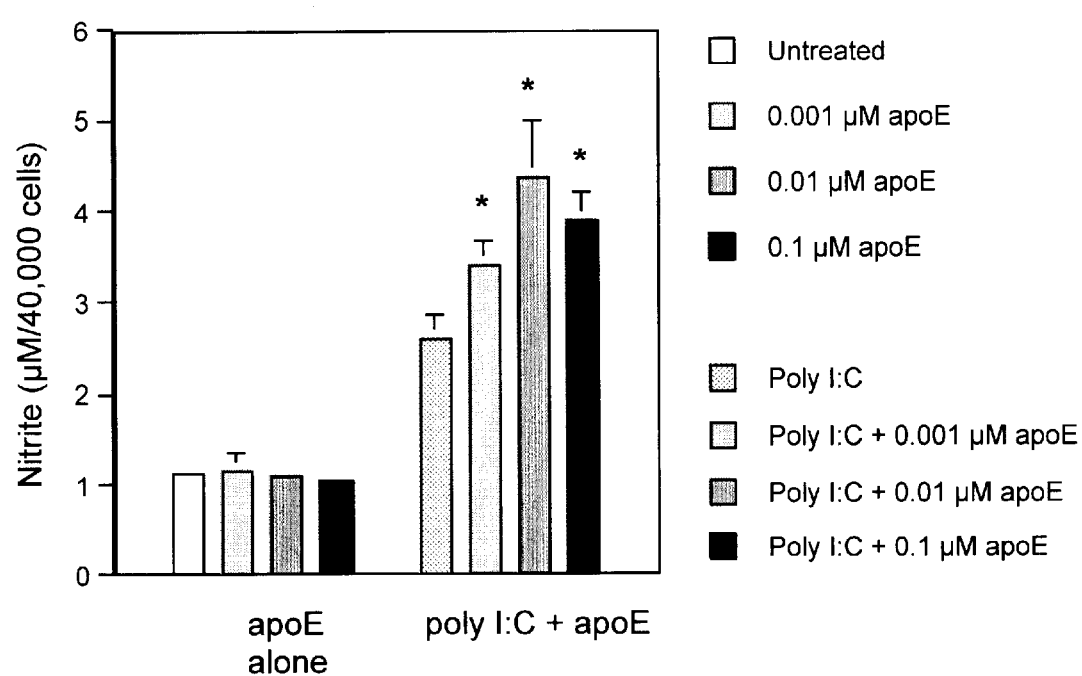

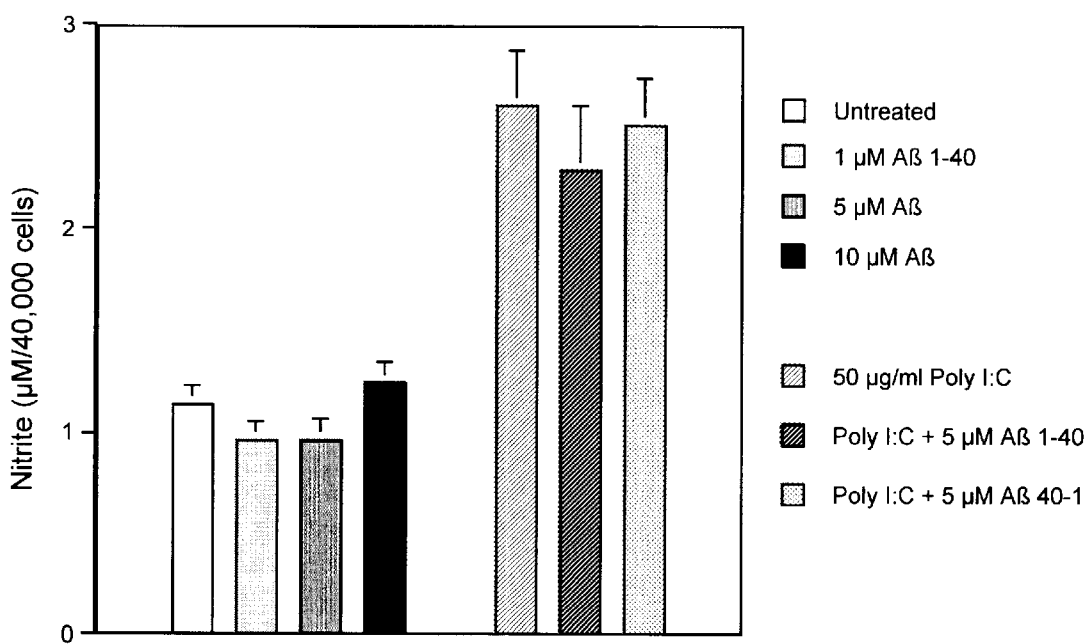
Figure 2. The effect of amyloid-ßeta peptides on nitrite production in human monocyte-derived macrophages.

Figure 3. Combination of apoE and Aß 1-40 on supernatant nitrite levels.
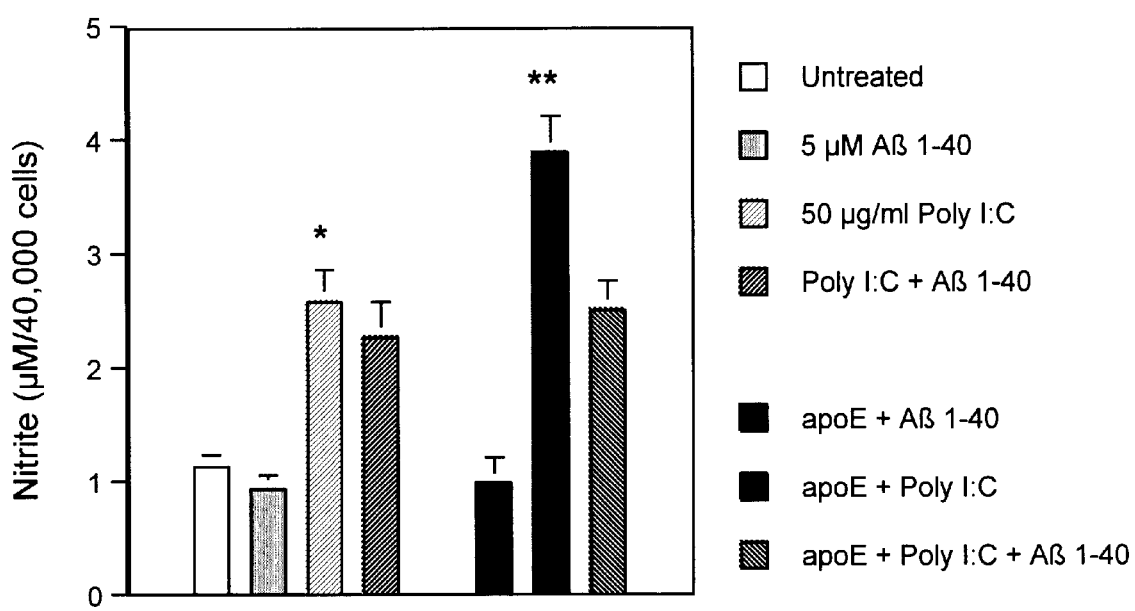

MODULATION OF NITRIC OXIDE PRODUCTION

This invention was made with Government support under Grant Number AG 12851 from the National Institute of Aging. The Government has certain rights to this invention.

FIELD OF THE INVENTION

This invention relates to methods of treatment carried out by increasing nitric oxide levels in cells in need thereof, such as cells that is heterozygous or homozygous for the APOE4 allele.

BACKGROUND OF THE INVENTION

As the major risk factor for late-onset Alzheimer's Disease, about 40% of all Alzheimer's cases are linked to the presence of an APOE4 allele [Saunders, A. M. et al., Neurology 44, 2420–2421 (1994)]. The APOE locus on chromosome 19 encodes three isoforms of apolipoprotein-E whose abundance in healthy populations is approxiatmately 8% APOE2, 78% APOE3, and 14% APOE4 [Mahley, R, Science 240, 622–630 (1988)]. Although the exact biochemical mechanism connecting the presence of APOE4 with the neuronal dysfunction and death seen in the brains of Alzheimer's patients has yet to be resolved, we hypothesize that apolipoprotein-E (APOE) may function in an isoform-specific manner to regulate cell survival.

Not all apolipoproteins are present in the brain and liver transplant studies show that apolipoprotein-E is made locally in the brain. As the most abundant apoprotein in human brain, APOE is made at low levels by a wide variety of cell types including macrophages and their brain counterparts, microglia [Basu, S., et al., Proc. Natl. Acad. Sci. U.S.A. 78, 7545–7549 (1981); Uchihara, T. et al.,. Neurosci. Letts. 195, 5–8 (1995)]. Cerebrospinal fluid levels of APOE range from 5 to 250 nM where it exists as a mostly "bare" apoprotein and as an apoprotein/lipid complex or lipoprotein [Landen, M. et al., Dementia 7, 273–278 (1996)]. In the blood, circulating lipoprotein complexes are classified by their apoprotein content and buoyant density. APOE is most abundant in the very low density lipoproteins particles of the blood [Roheim, P. et al., Proc. Natl. Acad. Sci. U. S. A. 76, 4646–9 (1979)] whose equivalents in the brain are a matter of active investigation. APOE expression is also increased in neurons and astrocytes surrounding the site of brain lesions [Han, S. et al., Neuropathol. Exp. Neurol. 53, 535–544 (1994).]. Recent reports suggest that APOE3-containing lipoproteins support the neurite outgrowth associated with healthy neuronal function to a greater degree than APOE4-containing lipoproteins [Nathan, B. et al., Science 264, 850–852 (1994)]. Consistent with this role, Miyata and Smith [Nature Genetics 14, 55–61 (1996)] recently proposed an antioxidant function for APOE that is isoform-specific in its ability to protect neurons from oxidative challenge. Thus, APOE appears to be present both at the time of cell injury and at the sites of cell injury where it could either serve as part of the mechanism to protect against cell damage or as active participants in cell destruction.

Alzheimer's is a chronic neurodegenerative disease characterized by neuritic plaques in the patient's brain which contain apolipoprotein-E, fibrillar amyloid-βeta peptide, dystrophic neurites and activated microglia [Perlmutter, L. et al., Neurosci. Lttrs. 119, 32–36 (1990)]. Like other tissue macrophages, activated microglia release oxyradicals such as superoxide anion and nitric oxide (NO) in response to a variety of factors. Recent evidence, however, demonstrates that the production of oxyradicals by human macrophages significantly differs from those of rat or mouse macrophages [Colton, C. et al., Mol. Chem. Neuropathol. 28, 15–20 (1996)].

SUMMARY OF THE INVENTION

Using a human model for microglial function, monocyte-derived macrophages from volunteer donors, we have now directly tested whether APOE modulates NO production. Aβ has also been implicated as a toxic agent in Alzheimer's through a proposed mechanism of NO synthesis and release [Meda, L. et al., Nature 374, 647–650 (1995)]. Since Aβ forms stable complexes with APOE [Strittmatter, W. et al., Proc. Natl. Acad. Sci. U.S.A. 90, 8098–8102 (1993)], we have also investigated their effect of Aβ alone and in combination with APOE on NO production in human cells.

In view of the foregoing, a first aspect of the invention is, accordingly, a method of treating cells that carry at least one APOE4 allele. The method comprises increasing nitric oxide levels in the cells (e.g., by administering an exogenous source of nitric oxide to the cells) by an amount sufficient to combat the decrease of nitric oxide level associated with the presence of the APOE4 allele.

A second aspect of the invention is a method of increasing nitric oxide levels in cells in need thereof. The method comprises administering APOE to the cells in an amount sufficient to increase nitric oxide levels in the cells.

A third aspect of the present invention is the use of an exogenous nitric oxide source for the preparation of a formulation or medicament for increasing nitric oxide levels in cells.

A fourth aspect of the present invention is the use of APOE for the preparation of a formulation or medicament for increasing nitric oxide levels in cells.

The foregoing and other objects and aspects of the present invention are explained in detail in the drawings herein and the specification set forth below.

BRIEF DESCRIPTION OF THE DRAWINGS

FIG. 1. The effect of apolipoprotein-E on nitrite production in cultured human monocyte-derived macrophage cells. The average nitrite production (±SEM) was obtained for monocyte-derived macrophages treated with varying concentrations of apolipoprotein-E alone and in combination with 50 µg/ml polyinosinic:polycytidylic acid (Poly I:C) for 5 days. * indicates significance of $p<0.002$ using ANOVA.

FIG. 2. The effect of amyloid-βeta peptides on nitrite production in human monocyte-derived macrophages. Average supernatant values (±SEM) for nitrite were determined for cultured human monocyte-derived macrophages treated with varying concentrations of Aβ peptides for 5 days in the presence and absence of 50 µg/ml Poly I:C. The first group of 4 bars (Untreated, 1 µM Aβ 1–40, 5 µM Aβ 1–40 and 10 µM Aβ 1–40) are not significantly different from one another. The second group of 3 bars (50 µg/ml Poly I:C, Poly I:C+5 µM Aβ 1–40 and Poly I:C+5µM Aβ 40–1) are not significantly different from one another. The first and second groups are significantly different from one another.

FIG. 3. Combination of APOE and Aβ 1–40 on supernatant nitrite levels. Cultured human monocyte-derived macrophages were either untreated or treated for 5 days with 5 µM Aβ 1–40 alone; 50 µg/ml Poly I:C alone; 5 µM Aβ 1–40 plus 50 µg/ml Poly I:C; or 50 µg/ml Poly I:C plus 10 nM APOE plus 5 μM Aβ 1–40. Data points represent the average supernatant level of nitrite (±SEM) from four wells of monocyte-derived macrophages assayed per experimental condition from at least four individuals.

DETAILED DESCRIPTION OF THE INVENTION

As noted above, a first aspect of the invention is a method of treating cells that carry at least one APOE4 allele. The method comprises increasing nitric oxide levels in the cells by an amount sufficient to combat the decrease of nitric oxide level associated with the presence of the APOE4 allele. The cells may, for example, be macrophages or glia cells (e.g., astrocytes, microglia, oligodendroglia). As explained further below, the cells are treated for the purpose of combatting or inhibiting the effects of stress, particularly oxidative stress, on the cells (that is, combatting or inhibiting the deleterious oxidative effects of oxy-radicals or oxidants in the cells) and thereby prolonging the life and/or enhancing the normal functioning of the cells being treated.

The method of the present invention may be carried out on cells in vitro, such as tissue culture cells to prolong the life of the cells in culture or cells that have been removed from a patient for manipulation and are to be returned to the patient. The method may also be carried out on cells in vivo in a patient in need of such treatment, such as a patient aflicted with Alzheimer's disease, HIV dementia, multiple sclerosis, amyotropic lateral sclerosis, rheumatoid arthritis, or inflammatory bowel disease.

The increasing step may be carried out by any suitable means, such as by administering an exogenous source of nitric oxide to the cells. Examples of suitable exogenous sources of nitric oxide include, but are not limited to, nitroglycerine, L-argenine, nitrate esters, isoamylynitrite, SIN-1, cysteine, dithiothreitol, N-acetylcysteine, mercaptosuccinic acid, thiosalicylic acid, and methylthiosalicylic acid. Numerous such compounds are known, and additional examples may be found in U.S. Pat. No. 5,543,430 to Kaesemeyer, U.S. Pat. No. 4,954,526 to Keefer, and U.S. Pat. No. 5,039,705 to Keefer et al. (Applicant intends that all U.S. Patent references cited herein are to be incorporated by reference herein in their entirety). The dosage of such compounds will be known or apparent to those skilled in the art, and will vary depending upon whether the cells are in vitro or in vivo, and on the route of in vivo administration. For example, L-arginine may be administered in vitro in the tissue culture solution containing the cells in an amount of from 2.5 to 40 or 60% w/v (g/ml), or may be administered intraveneously to a subject as a pharmaceutical grade of L-arginine in sterile water, buffer or saline solution in an amount of from 2.5 to 40 or 60% w/v (g/ml), with a typical dose of about 30 grams of L-arginine in sterile water (total volume 300 cc).

In one embodiment, the exogenous source of nitric oxide is a mixed ligand metal complex of a nitric oxide-nucleophile adduct, such as a compound of the formula KA, wherein:

A is $[(M)_x^{x'}(L)_y(R_1R_2N-N_2O_2)_z]$, and

M is a physiologically acceptable salt, or where x is at least two, a mixture of two different physiologically acceptable metals;

L is a ligand bound to at least one metal selected from the group consisting of $C_1$–$C_{20}$ alkoxy, $C_1$–$C_{20}$ carboxylate, $C_1$–$C_{20}$ alcohol, amino, $C_1$–$C_{20}$ alkyl amine, $C_1$–$C_{20}$ ether, $C_1$–$C_{20}$ ester, $C_1$–$C_{20}$ aminde, a sulfur or phosphorus containing ligand, a substituted derivative of any of the above, a halide, ammonia, an aquo, a hydroxo and an oxo ligand;

$R^1$ and $R^2$ may be the same or different and are selected from the group consisting of loweralkyl, aryl, and arylalkyl;

x is an integer of from 1 to 10, inclusive;

x' is the formal oxidation state of the metal M, and is an integer of from 1 to 6 inclusive;

y is an integer of from 1 to 18, inclusive, and where y is at least 2, the ligands L may be the same or different;

z is an integer of from 1 to 20, inclusive;

preferably with the first proviso that where M is copper, x is one, L is methanol and y is one, that at least one of $R^1$ and $R^2$ is not ethyl; and preferably with the second proviso that where L is aquo and x is one, that M is not sodium, potassium, calcium or nickel. K is a pharmaceutically acceptable counterion present in the composition when the overall charge of A is not zero, counterion K being present only in an amount to neutralize A. A specific example of such a compound is $EtNH^-[Cu(OAc)_3(Et_2N-N_2O_2)_2]$, where "Et" means ethyl and "OAc" refers to an acetate group. Such compounds may be made and used as described in U.S. Pat. No. 5,389,675 to Christodoulou et al., the disclosure of which is to be incorporated by reference herein in its entirety. In general, such compounds are administered so that the concentration thereof in a tissue culture solution containing cells in vitro is between about $10^{-11}$ or $10^{-10}$ to $10^{-5}$ Molar, or, when administered to cells in vivo, to achieve concentrations in the intracellular space surrounding the cells of about $10^{-11}$ or $10^{-10}$ to $10^{-5}$ Molar.

In another embodiment, the exogenous source of nitric oxide may be exogenously supplied nitric oxide synthase, which may be provided by transforming the cells in vitro or in vivo (or by transforming cells in vitro and then administering the cells back into a subject) with an inducible nitric oxide synthase gene in a suitable vector, such as described in U.S. Pat. No. 5,658,565 to Billiar et al., the disclosure of which is incorporated by reference herein in its entirety, and modifications thereof that will be apparent to those skilled in the art.

Also disclosed is a method of increasing nitric oxide levels in cells in need thereof. The method comprises administering APOE to the cells in an amount sufficient to increase nitric oxide levels in the cells. The APOE can be APOE2, APOE3, APOE4 or a combination thereof. Preferably, the APOE is APOE2, APOE3. The method may be carried out on any of the cells in vitro and in vivo of any of the types, and for any of the reasons, noted above.

APOE variants and fragments that bind to an APOE receptor are included within this definition of APOE. APOE can be from any species of origin, preferably of mammalian origin, more preferably human origin. The APOE molecules can be in a lipidated or delipidated state, with delipidated being preferred. APOE can be purified from natural sources (i.e., blood, serum or peritoneal fluid). Co-pending U.S. Application Ser. No. 08/539,328 describes the isolation of native APOE from peritoneal fluid, the disclosure of which is incorporated herein in its entirety by reference. The majority of APOE from sera is associated with lipoprotein particles. Purification of APOE from sera requires delipidation with organic solvents or detergents, which causes significant protein denaturation. Lipoprotein isolation by ultracentrifugation, with subsequent lyophilization and delipidation of lipoproteins, and chromatographic isolation of APOE, is described in Rall et al., (1986) *E. Methods Enzymol.* 128, 273. An alternative method for isolation of APOE from a mixture of apolipoproteins utilizes gel electrophoresis. Purification of APOE isoforms may be accomplished using isoelectric focusing techniques (Rall et al., (1986) E. Methods Enzymol. 128, 273). APOE may also be separated from contaminating proteins using heparin-sepharose chromatography, which utilizes the heparin-binding property of APOE. Rall et al., (1986) E. Methods Enzymol. 128, 273. APOE may be isolated and/or purified, optionally to homogeneity, by conventional techniques such as affinity chromatography, size-exclusion chromatography, gas chromatography, HPLC, and combinations thereof. Separation of the non-cysteine containing E4 isoform of APOE from contaminating cysteine-containing proteins may be accomplished using thiopropyl chromatography on thiopropyl Sepharose (Weisgraber et al. (1983), J. Biol. Chem. 258, 2508). Recombinant APOE can be produced using methods known in the art, and human recombinant APOE is commercially available. However, recombinant protein is not in the native glycosylated form and is subject to denaturation and oxidation during purification. The APOE may be administered to cells in vitro in by adding from about 0.001 uM to about 0.1 or 0.1 uM of APOE to a tissue culture solution containing the cells, or may be administered to cells in vivo by administering the APOE by any suitable route of administration so as to achieve a concentration of APOE in the intracellular spaces of from about 0.001 uM to about 0.1 or 1 uM.

The genotype of cells or patients for the APOE allele may be determined by any suitable technique, including both DNA amplification of the APOE allele and by analytical chemistry of APOE protein, as described in U.S. Pat. No. 5,508,167 to Roses et al.

The present invention is explained in greater detail in the following non-limiting Examples.

EXAMPLES

The following abbreviations are used herein: APOE, apolipoprotein-E protein; Aβ, amyloid-βeta peptide; NO, nitric oxide; poly I:C, polyinosinic:polycytidylic acid; APOE, apolipoprotein-E gene; APOE2, APOE3, APOE4, epsilon 2, epsilon 3 and epsilon 4 alleles of the APOE gene; MDM, monocyte-derived macrophage cells; L-NMMA, N-G-methyl-1-arginine; gamma-IFN, gamma interferon.

I. Methods

Cell Cultures: Human monocytes from normal, adult volunteers were generously provided by Dr. D. Webb, Center for Biologics Evaluation and Research, NIH, Bethesda, Md. Elutriated monocytes were cultured in Dulbecco's Modified Eagle Medium (DMEM) containing 20% fetal calf serum, 10% human Aβ serum (ABI Technologies, Columbia, Md.) and 20 µg/ml human M-Colony Stimulating Factor (M-CSF, Genzyme, Boston, Mass.) at 37° C. in a humidified atmosphere of 5% $CO_2$, 95% air. After 5 to 7 days, morphological changes including spreading and branching of the cells signaled differentiation from monocytes to macrophages and are now commonly called "Monocyte-Derived Macrophages" (MDMs). MDM cells were removed from the flasks by gentle trypsinization, plated at 40,000 cells/well into 96 well microtiter plates and allowed to recover overnight. These MDM cells were then primed by exposure to 1000 U/ml recombinant human gamma interferon (gamma-IFN, Sigma Chemical Co., St. Louis, Mo.) diluted into HL-1 serum free media (Hycor Biomedical Include, Irvine, Calif.). At the end of 12 h priming with gamma-IFN, the priming media was replaced with HL-1 serum free media before experimental treatments as listed in the text. Following experimental treatments, the media was removed and assayed for nitrite levels using the Griess reaction [Colton, C. et al., Mol. Chem. Neuropathol. 28, 15–20 (1996)].

Treatment Factors and Conditions: M-CSF-differentiated and gamma-IFN-primed monocyte-derived macrophage cells were treated by incubation with varying concentrations of Aβ 1–40, its reverse sequence Aβ 40–1 and a non-toxic Aβ fragment, Aβ 1–28 (Bachem, Torrance, Calif.). Aβ peptides were diluted into sterile, double-distilled water and allowed to aggregate at room temperature for 48 h and then stored at −80° C. until use. Human apolipoprotein-E purified protein (Chemicon International, Inc., Temecula, Calif.) was reconstituted in serum free media and added to cells. The double stranded polyribonucleotide, polyinosinic:polycytidylic acid (poly I:C potassium salt, Sigma Chemical Co., St. Louis, Mo.) was also reconstituted into serum free media and used to stimulate nitric oxide (NO) production as described by J. Snell et al., Journal of Leukocyte Biology, 62, 369 (1997).

Measurement of Nitric Oxide (NO): After treatment, conditioned media was removed from cells and the level of nitrite, which is a stable end-product of NO release in biological systems, measured using the Griess reaction [Colton, C., supra]. Briefly, conditioned media were transferred to a new 96 well microtiter plate and an equal volume of Griess reagents were added to each well. After 10 minutes of incubation at room temperature, color development was assessed at 550 nm using a plate reader. Nitrite levels are presented as $\mu$M/well which contained 40,000 cells and an average (±SEM) obtained for at least 4 wells assayed per experimental condition for each of at least 4 individual donors. Treatment with the nitric oxide synthase (NOS) inhibitor, N-G-methyl-1-arginine (L-NMMA) was used to determine the level of NOS-mediated NO production. Statistical significance was determined using a one way analysis of variance (ANOVA).

II. Results

We tested whether apolipoprotein-E (APOE) and/or amyloid-βeta peptide (Aβ) might stimulate oxy-radical production in gamma-interferon (gamma-IFN) primed Monocyte-Derived Macrophages (MDMs). In FIG. 1, gamma-IFN-primed MDMs were treated with APOE in concentrations ranging from 1 nM to 100 nM for 5 days and the conditioned media assayed for nitrite content as an indirect measure of their NO production. Compared to untreated controls, no significant increase of nitrite levels was observed with APOE treatment alone. In contrast, MDM exposed to 50 µg/ml of the double-stranded polyribonucleoside poly I:C stimulated a 126% increase in nitrite levels as we have recently reported [Vouldoukis, I. et al., Proc. Natl. Acad. Sci. U.S.A. 92, 7804–7808 (1995)]. When poly I:C was added together with 10 nM APOE, a significant increase in nitrite levels of 68% (p<0.009) was measured compared to poly I:C alone, which combines for an overall increase of 282% compared to untreated or APOE-alone treated MDMs. This effect appears to require non-denatured APOE as treatment with poly I:C and boiled APOE gave nitrite levels similar to poly I:C alone (data not shown). This effect also appears to depend on the enzymatic activity of Nitric Oxide Synthase (NOS) to produce NO de novo as treatment with the L-NMMA, an inhibitor of NOS, reduced nitrite levels to those seen in the unstimulated controls (data not shown).

A similar analysis was performed for the amyloid-βeta peptide fragments of the Amyloid Precursor Protein (APP). As above, we treated gamma-IFN-primed MDM's with the toxic Aβ 1–40 fragment of APP which is found in fibrillar plaques of Alzheimer's patients' brains, a non-toxic Aβ 1–28 fragment and the reverse peptide control, Aβ 40–1. Compared to untreated human MDMs, no significant change in nitrite levels was measured following treatment with 1 to 10 μgM of any of these peptides (FIG. 2). Unlike APOE, when 50 μg/ml poly I:C was combined with Aβ peptide treatments, no significant increase in nitrite levels was measured compared to poly I:C alone (FIG. 2).

Since Aβ and human APOE form stable complexes [Strittmatter, W. et al., *Proc. Natl. Acad. Sci. USA.* 90, 8098–8102 (1993)], then the possibility exists that the APOE/Aβ complex might have properties distinct from each of it component parts. To test this idea, we treated human MDMs with a combination of Aβ 1–40, APOE and poly I:C and found no significant difference in the nitrite levels compared to poly I:C treatment alone (FIG. 3). This suggests that Aβ blocked the APOE potentiation of NO production. The same result was obtained when the amyloidogenic, but non-toxic Aβ 1–28 was substituted for Aβ 1–40 (data not shown). The combination of Aβ 1–40 and APOE in the absence of poly I:C had no significant effect on nitrite levels compared to untreated control MDMs.

III. Discussion

The induction of oxidative stress appears to play a role in chronic neurodegenerative disease and evidence of oxidation in the brains of patients with Alzheimer's has been demonstrated [Mecocci, P. et al., *Ann. Neurol.* 36, 747–51 (1994); Smith, M. et al., *J Neurochem.* 64, 2660–2666 (1995); Good, P. et al., *Am. J Path.* 149, 21–28 (1996)]. Smith et al. [*Nature* 382, 120–121 (1996)] report that the regions known to be affected in AD brains contain more oxidation-byproducts, including nitrotyrosine and carbonyls, than similar regions from age-matched healthy controls. Although the exact mechanism generating these oxidized products is unknown, the microglia associated with neuritic plaques appear to be activated. In addition to proteases, cytokines and APOE [Eikelenboom, P. and Veerhuis, R., *Neurobiol. Aging* 17, 673–80 (1996)], activated microglia are well known to release oxy-radicals further suggesting that they play a critical role in the development of oxidative stress.

Oxidative stress occurs when oxidant levels are higher than the cell's antioxidant defenses against them. Based on the work of Meda et al. [*Nature* 374, 647–650 (1995)] where mouse microglial cells exposed to Aβ released nitric oxide, we expected that Aβ treatment of human cells would also stimulate the release of nitric oxide. We found that Aβ failed to stimulate nitric oxide production in human macrophages (FIG. 2). Instead, we found that human macrophages treated with APOE and poly I:C released 68% more NO than cells treated with poly I:C alone and almost 3 fold more NO than unprimed cells. This increase is inhibitable with a competitive NOS inhibitor, L-NMMA, suggesting de novo production of NO accounts for the increased nitrite levels. Although these results were unexpected, they confirm that human cells are capable of responding to stimuli and strengthen the concept that a human response to stimulation is very different from a rat or mouse response. The most noticeable difference is the failure of Aβ to stimulate NO production in human cells. Even if NO had been made, the amount of NO produced by maximally activated human macrophages has been measured in the 1 to 5 μM range compared to 50 to 100 μM in rodent macrophages [Colton, C. et al., *Mol. Chem. Neuropathol.* 28, 15–20 (1996)]. While cytokines like Interleukin-1 or inflammatory mediators like LPS stimulate NO release in rodent cells, the activation of iNOS (inducible NOS) in human macrophages is independent of cytokines like IL-1 and instead, depends on the cross-linking of specific membrane receptors for induction [Vouldoukis, I. et al., *Proc. Natl. Acad. Sci. U.S.A.* 92, 7804–7808 (1995)].

Our novel finding that apolipoprotein-E increases nitric oxide production suggests that APOE-mediated signaling modulates Nitric Oxide Synthase (NOS). Our data further suggests that cell-surface receptors are involved in this induction. Several different receptor systems found on macrophages can directly bind to APOE and/or lipoprotein complexes containing APOE. These include the apoB/E receptor more commonly known as the LDL receptor (Low Density Lipoprotein receptor), the LRP receptor encoded on chromosome 12 and the new, type II, APOE receptor [Kim, D. et al., *J. Biol. Chem.* 271, 8373–8380 (1996)]. Macrophage scavenger receptors may also be involved since superoxide released from activated macrophages easily generates oxidized-lipoproteins which avidly bind to this class of receptors [El Khoury, J. et al., *Nature* 382, 716–719 (1996)]. Similarly, glyco-oxidized proteins and lipid may bind the scavenger receptor and the RAGE receptor found on many cell types [Yan, S. et al., *Nature* 382, 685–691 (1996)]. Based on the demonstration that antibody-mediated cross-linking of CD23 receptors stimulates NO production in human macrophages [Vouldoukis, I. et al., *Proc. Natl. Acad. Sci. U.S.A.* 92, 7804–7808 (1995)], we hypothesize that one or more of these cell surface receptors must be directly involved in the APOE-mediated induction of NOS. This hypothesis is supported for several reasons. First, APOE denatured by boiling is unable to increase NO production suggesting that non-boiled APOE which can bind to receptors is required to produce the effect. Second, APOE3 protein is normally found as dimers and tetramers which like divalent antibodies, could cross-link at least 2 separate receptor molecules. Third, macrophages treated with a combination of APOE, Aβ and poly I:C produce the same amount of NO as cells treated with only poly I:C. Since APOE and Aβ can rapidly form stable complexes, it is likely that these complexes may be unable to stimulate the NO production seen with APOE and poly I:C treatment. This result could be easily explained if the APOE-Aβ complex is unable to bind to cellular receptors or, like an pharmacological antagonist, binds and fails to activate the receptor. Alternatively, APOE-mediated stimulation of NO production may depend upon internalization and binding to internal receptor targets, both of which may be inhibited in the presence of Aβ.

In summary, we describe a novel function for apolipoprotein-E in modulating nitric oxide production by human macrophages. This effect appears to be a receptor-mediated mediated event and isoform-specific binding of APOE protein to receptors has been reported [van Vlijmen, B. J. et al., *J Biol. Chem.* 271, 30595–30602 (1996]. Combined with genetic studies showing that Alzheimer's disease is strongly associated with the presence of the APOE4 allele, these data predict isoform-specific effects of APOE protein in modulating NO production.

The foregoing is illustrative of the present invention, and is not to be construed as limiting thereof. The invention is defined by the following claims, with equivalents of the claims to be included therein.

We claim:

1. A method of treating a subject afflicted with Atzheimer's disease, comprising the steps of:

determining whether or not said subject carries at least one APOE4 allele, and then, if said subject carries at least one APOE4 allele, increasing nitric oxide levels in cells of said subject by an amount sufficient to combat the decrease of nitric oxide level associated with the presence of said at least one APOE4 allele;

wherein said exogenous source of nitric oxide is selected from the group consisting of nitroglycerine, L-arginine, nitrate esters, isoamylynitrite, S-nitro-N-cysteine (SIN-1); and, cysteine, dithiothreitol, N-acetylcysteine, mercaptosuccinic acid, thiosalicyclic acid, and methylthiosalicylic acid.

2. A method of treating a subject afflicted with Alzheimer's disease, comprising the steps of:

determining whether or not said subject carries at least one APOE4 allele, and then, if said subject carries at least one APOE4 allele, increasing nitric oxide levels in cells of said subject by an amount sufficient to combat the decrease of nitric oxide level associated with the presence of said at least one APOE4 allele;

wherein said increasing step is carried out by administering an exogenous source of nitric oxide to said subject;

and wherein said exogenous source of nitric oxide is a mixed ligand metal complex of a nitric oxide-nucleophile adduct of the formula KA, wherein:

A is $[(M)_x^{x'}(L)_y(R_1R^2N-N_2O_2)_2]$, and

M is a physiologically acceptable salt, or where x is at least two, a mixture of two different physiologically acceptable metals;

L is a ligand bound to at least one metal selected from the group consisting of $C_1$–$C_{20}$ alkoxy, $C_1$–$C_{20}$ carboxylate, $C_1$–$C_{20}$ alcohol amino, $C_1$–$C_{20}$ alkyl amine, $C_1$–$C_{20}$ ether, $C_1$–$C_{20}$ ester, $C_1$–$C_{20}$ aminde, a sulfur or phosphorus containing ligand, a halide, ammonia, an aquo, a hydroxo and an oxo liqand;

$R^1$ and $R^2$ may be the same or different and are selected from the group consisting of loweralkyl, aryl, and arylalkyl;

x is an integer of from 1 to 10, inclusive;

x' is the formal oxidation state of the metal M, and is an integer of from 1 to 6 inclusive;

y is an integer of from 1 to 18, inclusive, and where y is at least 2, the ligands L may be the same or different;

z is an integer of from 1 to 20, inclusive, and

K is a pharmaceutically acceptable counterion present in the composition when the overall charge of A is not zero.

3. The method according to claim 1, wherein said exogenous source of nitric oxide is nitroglycerine.

4. The method according to claim 1, wherein said exogenous source of nitric oxide is L-argenine.

5. The method according to claim 1, wherein said exogenous source of nitric oxide is a nitrate ester.

6. The method according to claim 1, wherein said exogenous source of nitric oxide is isoamylynitrite.

7. The method according to claim 1, wherein said exogenous source of nitric oxide is SIN-1.

8. The method according to claim 1, wherein said exogenous source of nitric oxide is cysteine.

9. The method according to claim 1, wherein said exogenous source of nitric oxide is dithiothreitol.

10. The method according to claim 1, wherein said exogenous source of nitric oxide is N-acetylcysteine.

11. The method according to claim 1, wherein said exogenous source of nitric oxide is mercaptosuccinic acid.

12. The method according to claim 1, wherein said exogenous source of nitric oxide isthiosalicyclic acid.

13. The method according to claim 1, wherein said exogenous source of nitric oxide is methylthiosalicyclic acid.

14. The method according to claim 2, wherein said exogenous source of nitric oxide is $EtNH^+[Cu(Oac)_3(Et_2N-N_2O_2)_2]^-$.

* * * * *

UNITED STATES PATENT AND TRADEMARK OFFICE
CERTIFICATE OF CORRECTION

PATENT NO.    : 6,436,996 B1
DATED         : August 20, 2002
INVENTOR(S)   : Vitek et al.

It is certified that error appears in the above-identified patent and that said Letters Patent is hereby corrected as shown below:

Column 9,
Line 25, should read as follows: -- A is $[(M)_x^{x'}(L)_y(R^1R^2N\text{---}N_2O_2)_z]$, and --

Signed and Sealed this

Fifteenth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,436,996 B1 Page 1 of 1
APPLICATION NO. : 08/940594
DATED : August 20, 2002
INVENTOR(S) : Vitek et al.

It is certified that error appears in the above-identified patent and that said Letters Patent is hereby corrected as shown below:

Col. 9, lines 5-6, claim 1: "(SIN-1); and, cysteine," should read --(SIN-1), cysteine--

Signed and Sealed this

Twelfth Day of August, 2008

JON W. DUDAS
*Director of the United States Patent and Trademark Office*